United States Patent
Coburn et al.

(10) Patent No.: US 7,329,746 B2
(45) Date of Patent: Feb. 12, 2008

(54) MACROCYCLIC BETA-SECRETASE INHIBITORS FOR THE TREATMENT OF ALZHEIMER'S DISEASE

(75) Inventors: Craig A. Coburn, Royersford, PA (US); Shawn J. Stachel, Perkasie, PA (US); Joseph P. Vacca, Telford, NJ (US)

(73) Assignee: Merck & Co., Inc., Rahway, NJ (US)

( * ) Notice: Subject to any disclaimer, the term of this patent is extended or adjusted under 35 U.S.C. 154(b) by 8 days.

(21) Appl. No.: 10/568,153

(22) PCT Filed: Aug. 10, 2004

(86) PCT No.: PCT/US2004/025791

§ 371 (c)(1),
(2), (4) Date: Feb. 13, 2006

(87) PCT Pub. No.: WO2005/018545

PCT Pub. Date: Mar. 3, 2005

(65) Prior Publication Data

US 2007/0037784 A1    Feb. 15, 2007

Related U.S. Application Data

(60) Provisional application No. 60/495,667, filed on Aug. 14, 2003.

(51) Int. Cl.
| C07D 225/04 | (2006.01) |
| C07D 267/22 | (2006.01) |
| A61K 31/33  | (2006.01) |
| A61K 31/395 | (2006.01) |
| A61P 25/28  | (2006.01) |

(52) U.S. Cl. ............ 540/453; 540/461; 540/466; 540/453; 514/337; 514/339

(58) Field of Classification Search .......... None
See application file for complete search history.

(56) References Cited

U.S. PATENT DOCUMENTS 6,333,410 B1    12/2001   Chari et al.

FOREIGN PATENT DOCUMENTS

| WO | WO 03/106405   | 12/2003 |   |
| WO | WO 2005/005374 | 1/2005  |   |
| WO | WO2005/018545  | * | 3/2005 |
| WO | WO2005018545   | * | 3/2005 |

OTHER PUBLICATIONS

Olah et al. Journal of Organic Chemistry, 1993, 58, 3194-3195.*
Coburn et al. Bioorganic and Medicinal Chemistry Letters, 2006, 16, 3635-3638.*
Hull et al. Drugs, 2006, 66(16), 2075-2093.*
Garino et al. Journal of Medicinal Chemistry, 2006, 49, 4275-4285.*

* cited by examiner

*Primary Examiner*—James O. Wilson
*Assistant Examiner*—Noble Jarrell
(74) *Attorney, Agent, or Firm*—William Krovatin; John C. Todaro

(57) ABSTRACT

The present invention is directed to compounds of formula I which are inhibitors of the beta-secretase enzyme and that are useful in the treatment or prevention of diseases in which the beta-secretase enzyme is involved, such as Alzheimer's disease. The invention is also directed to pharmaceutical compositions comprising these compounds and the use of these compounds and compositions in the prevention or treatment of such diseases in which the beta-secretase enzyme is involved

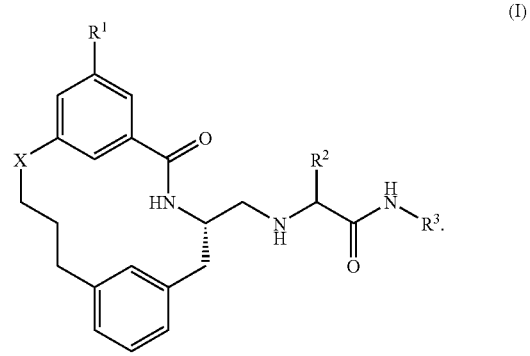

16 Claims, No Drawings

MACROCYCLIC BETA-SECRETASE INHIBITORS FOR THE TREATMENT OF ALZHEIMER'S DISEASE

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

CROSS-REFERENCE TO RELATED APPLICATIONS

This application claims priority under 35 U.S.C. § 119(e) from Provisional Application Ser. No. 60/495,667, filed Aug. 14, 2003.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein ($\beta$A4, also referred to as A$\beta$, $\beta$-protein and $\beta$AP) which is a proteolytic product of a precursor protein of much larger size. The amyloid precursor protein (APP or A$\beta$PP) has a receptor-like structure with a large ectodomain, a membrane spanning region and a short cytoplasmic tail. The A$\beta$ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative $\alpha$-secretase which cleaves within the A$\beta$ protein to release $\alpha$-$APP_s$ and precludes the release of intact A$\beta$. A minor portion of $APP_s$ is released by a $\beta$-secretase ("$\beta$-secretase"), which cleaves near the $NH_2$-terminus of APP and produces COOH-terminal fragments (CTFs) which contain the whole A$\beta$ domain. Thus, the activity of $\beta$-secretase or $\beta$-site amyloid precursor protein-cleaving enzyme ("BACE") leads to the abnormal cleavage of APP, production A$\beta$, and accumulation of $\beta$ amyloid plaques in the brain, which is characteristic of Alzheimer's disease (see R. N. Rosenberg, Arch. Neurol., vol. 59, September 2002, pp. 1367-1368; H. Fukumoto et al, Arch. Neurol., vol. 59, September 2002, pp. 1381-1389; J. T. Huse et al, J. Biol. Chem., vol 277, No. 18, issue of May 3, 2002, pp. 16278-16284; K. C. Chen and W. J. Howe, Biochem. Biophys. Res. Comm, vol. 292, pp 702-708, 2002). Therefore, therapeutic agents that can inhibit $\beta$-secretase or BACE may be useful for the treatment of Alzheimer's disease.

The compounds of the present invention are useful for treating Alzheimer's disease by inhibiting the activity of $\beta$-secretase or BACE, thus preventing the formation of insoluble A$\beta$ and arresting the production of A$\beta$.

SUMMARY OF THE INVENTION

The present invention is directed to compounds that are inhibitors of the $\beta$-secretase enzyme that are useful in the treatment of diseases in which the $\beta$-secretase enzyme is involved, such as Alzheimer's disease. The invention is also directed to pharmaceutical compositions comprising these compounds and the use of these compounds and compositions in the prevention or treatment of such diseases in which the $\beta$-secretase enzyme is involved.

DETAILED DESCRIPTION OF THE INVENTION

The present invention is directed to compounds of the formula I:

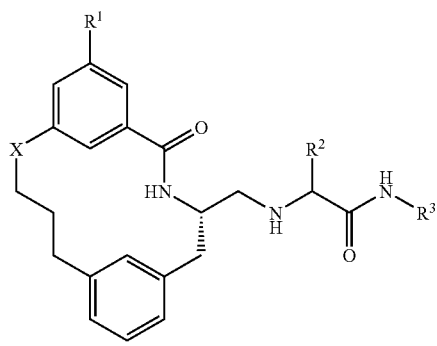

wherein:
$R^1$ is selected from the group consisting of:
  (1) hydrogen,
  (2) $R^4$—$S(O)_pN(R^5)$—,
    wherein $R^4$ is independently selected from the group consisting of:
      (a) —$C_{1-8}$alkyl, which is unsubstituted or substituted with 1-6 fluoro,
      (b) —$NR^5R^6$,
      (c) phenyl, and
      (d) benzyl,
    wherein $R^5$ and $R^6$ are independently selected from the group consisting of:
      (a) hydrogen,
      (b) —$C_{1-6}$alkyl, which is unsubstituted or substituted with 1-6 fluoro,
      (c) phenyl, and
      (d) benzyl,
    and wherein p is independently 0, 1, or 2,
  (3) —CN,
  (4) —$C_{1-6}$alkyl-CN,
  (5) halogen,
  (6) phenyl, which is unsubstituted or substituted with 1-5 substituents where the substituents are independently selected from:
      (a) —CN,
      (b) halo,
      (c) —$C_{1-6}$alkyl,
      (d) —O—$R^5$,
      (e) —$CO_2R^5$, and
      (f) —$C(O)R^5$, (7)

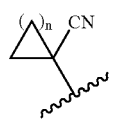

wherein n is 1, 2, 3 or 4;

$R^2$ is selected from the group consisting of:
(1) hydrogen,
(2) —$C_{1-6}$alkyl, —$C_{2-6}$alkenyl, —$C_{2-6}$alkynyl, or —$C_{3-8}$cycloalkyl which is unsubstituted or substituted with 1-7 substituents where the substituents are independently selected from:
  (a) halo,
  (b) hydroxy,
  (c) —O—$C_{1-6}$alkyl,
  (d) —$C_{3-6}$cycloalkyl,
  (e) —S(O)$_p$—$C_{1-6}$alkyl,
  (f) —CN,
  (g) —$CO_2$H,
  (h) —$CO_2$—$C_{1-6}$alkyl,
  (i) —CO—$NR^5R^6$,
  (j) phenyl, which is unsubstituted or substituted with 1-5 substituents where the substituents are independently selected from:
    (i) —$C_{1-6}$alkyl,
    (ii) —CN,
    (iii) halo,
    (iv) —$CF_3$,
    (v) —O—$R^5$, and
    (vi) —$CO_2R^5$,
(3) phenyl which is unsubstituted or substituted with 1-5 substituents where the substituents are independently selected from:
  (a) —$C_{1-6}$alkyl,
  (b) —CN,
  (c) halo,
  (d) —$CF_3$,
  (e) —O—$R^5$, and
  (f) —$CO_2R^5$;

$R^3$ is selected from the group consisting of:
(1) hydrogen,
(2) —$C_{1-6}$alkyl, —$C_{2-6}$alkenyl, —$C_{2-6}$alkynyl, or —$C_{3-8}$cycloalkyl which is unsubstituted or substituted with 1-7 substituents where the substituents are independently selected from:
  (a) halo,
  (b) hydroxy,
  (c) —O—$C_{1-6}$alkyl,
  (d) —$C_{3-6}$cycloalkyl,
  (e) phenyl or pyridyl, which is unsubstituted or substituted with 1-5 substituents where the substituents are independently selected from:
    (i) —$C_{1-6}$alkyl,
    (ii) —CN,
    (iii) halo,
    (iv) —$CF_3$,
    (v) —O—$R^5$, and
    (vi) —$CO_2R^5$,
  (f) —S(O)$_p$N($R^5$)—$C_{1-6}$alkyl, and
  (g) —S(O)$_p$N($R^5$)-phenyl,
(3) phenyl which is unsubstituted or substituted with 1-5 substituents where the substituents are independently selected from:
  (a) —$C_{1-6}$alkyl,
  (b) —CN,
  (c) halo,
  (d) —$CF_3$,
  (e) —O—$R^5$, and
  (f) —$CO_2R^5$;

X is selected from the group consisting of:
(1) —$CH_2$—, and
(2) —O—;

and pharmaceutically acceptable salts thereof.

An alternate embodiment of the present invention is directed to compounds of the formula I:

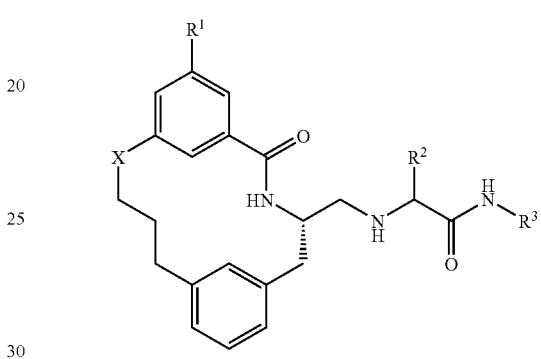

I wherein:
$R^1$ is selected from:
(1) $CH_3$—S(O)$_2$N($CH_3$)—;
(2) $CH_3CH_2$—S(O)$_2$N($CH_3$)—;
(3) ($CH_3$)$_2$CH—S(O)$_2$N($CH_3$)—;
(4) phenyl-S(O)$_2$N($CH_3$)—; and
(5) ($CH_3$)$_2$N—S(O)$_2$N($CH_3$)—;

$R^2$ is —$C_{1-6}$alkyl, unsubstituted or substituted with cyclopropyl or halo;

$R^3$ is —$C_{1-6}$alkyl or —$C_{3-8}$cycloalkyl; and

X is —$CH_2$— or —O—;

and pharmaceutically acceptable salts thereof.

A first embodiment of the present invention is directed to compounds of the formula II:

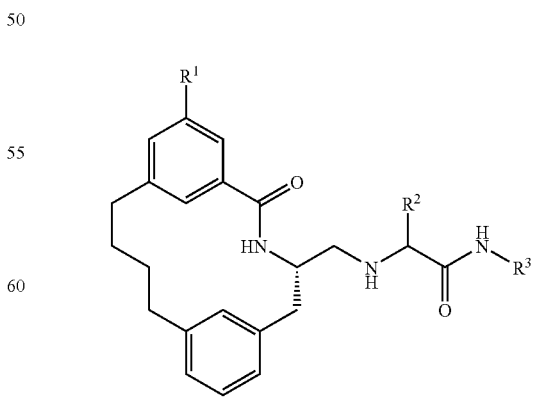

II wherein $R^1$, $R^2$, $R^3$ are as defined herein.

A second embodiment of the present invention is directed to compounds of the formula III:

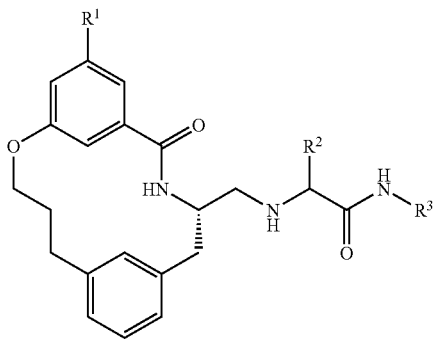

wherein $R^1$, $R^2$, $R^3$ are as defined herein.

In an embodiment of the present invention $R^1$ is $R^4$—S(O)$_2$N(R$^5$)—, wherein $R^4$ is independently selected from the group consisting of:
(a) —C$_{1-6}$alkyl, which is unsubstituted or substituted with 1-6 fluoro,
(b) phenyl, and
(c) benzyl, and wherein $R^5$ is independently selected from the group consisting of:
(a) hydrogen,
(b) —C$_{1-6}$alkyl, which is unsubstituted or substituted with 1-6 fluoro,
(c) phenyl, and
(d) benzyl.

In another embodiment of the present invention $R^1$ is selected from:
(1) CH$_3$—S(O)$_2$N(CH$_3$)—;
(2) CH$_3$CH$_2$—S(O)$_2$N(CH$_3$)—;
(3) (CH$_3$)$_2$CH—S(O)$_2$N(CH$_3$)—; and
(4) phenyl-S(O)$_2$N(CH$_3$)—;
(5) (CH$_3$)$_2$N—S(O)$_2$N(CH$_3$)—.

In a further embodiment of the present invention $R^1$ is CH$_3$—S(O)$_2$N(CH$_3$)—.

In an embodiment of the present invention $R^2$ is —C$_{1-6}$ alkyl, unsubstituted or substituted with cyclopropyl or halo.

In another embodiment of the present invention $R^2$ is selected from:
(1) CH$_3$—;
(2) CH$_3$CH$_2$—;
(3) (CH$_3$)$_2$CH—;
(4) CH$_3$CH$_2$CH$_2$—;
(5) (CH$_3$)$_2$CHCH$_2$—;
(6) CH$_3$CH$_2$CH$_2$CH$_2$—;
(7) CH$_3$CH$_2$CH$_2$CH$_2$CH$_2$—;
(8) cyclopropyl-CH$_2$—;
(9) CF$_3$CH$_2$—; and
(10) CH$_2$FCH$_2$—.

In an embodiment of the present invention $R^3$ is —C$_{1-6}$ alkyl or —C$_{3-8}$cycloalkyl.

In another embodiment of the present invention $R^3$ is selected from:
(1) CH$_3$—;
(2) CH$_3$CH$_2$—;
(3) (CH$_3$)$_2$CH—;
(4) CH$_3$CH$_2$CH$_2$—;
(5) (CH$_3$)$_2$CHCH$_2$—;
(6) CH$_3$CH$_2$CH$_2$CH$_2$—;
(7) CH$_3$CH$_2$CH$_2$CH$_2$CH$_2$—; and
(8) bicyclo[2.2.1]heptyl-.

In a further embodiment of the present invention $R^3$ is (CH$_3$)$_2$CHCH$_2$—.

A specific embodiment of the present invention includes a compound which is selected from the title compounds of the following Examples and pharmaceutically acceptable salts thereof.

The compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halo or halogen as used herein are intended to include fluoro, chloro, bromo and iodo. Similarly, C$_{1-6}$, as in C$_{1-6}$alkyl is defined to identify the group as having 1, 2, 3, 4, 5 or 6 carbons in a linear or branched arrangement, such that C$_{1-6}$alkyl specifically includes methyl, ethyl, n-propyl, iso-propyl, n-butyl, iso-butyl, tert-butyl, pentyl and hexyl. Likewise, C$_{3-8}$cycloalkyl includes cyclopropyl, cyclobutyl, cyclopentyl, cyclohexyl, cycloheptyl, cyclooctyl and bicyclic versions thereof. A group which is designated as being independently substituted with substituents may be independently substituted with multiple numbers of such substituents.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The compounds of the present invention are prepared by the methods outlined in Schemes 1 and 2.

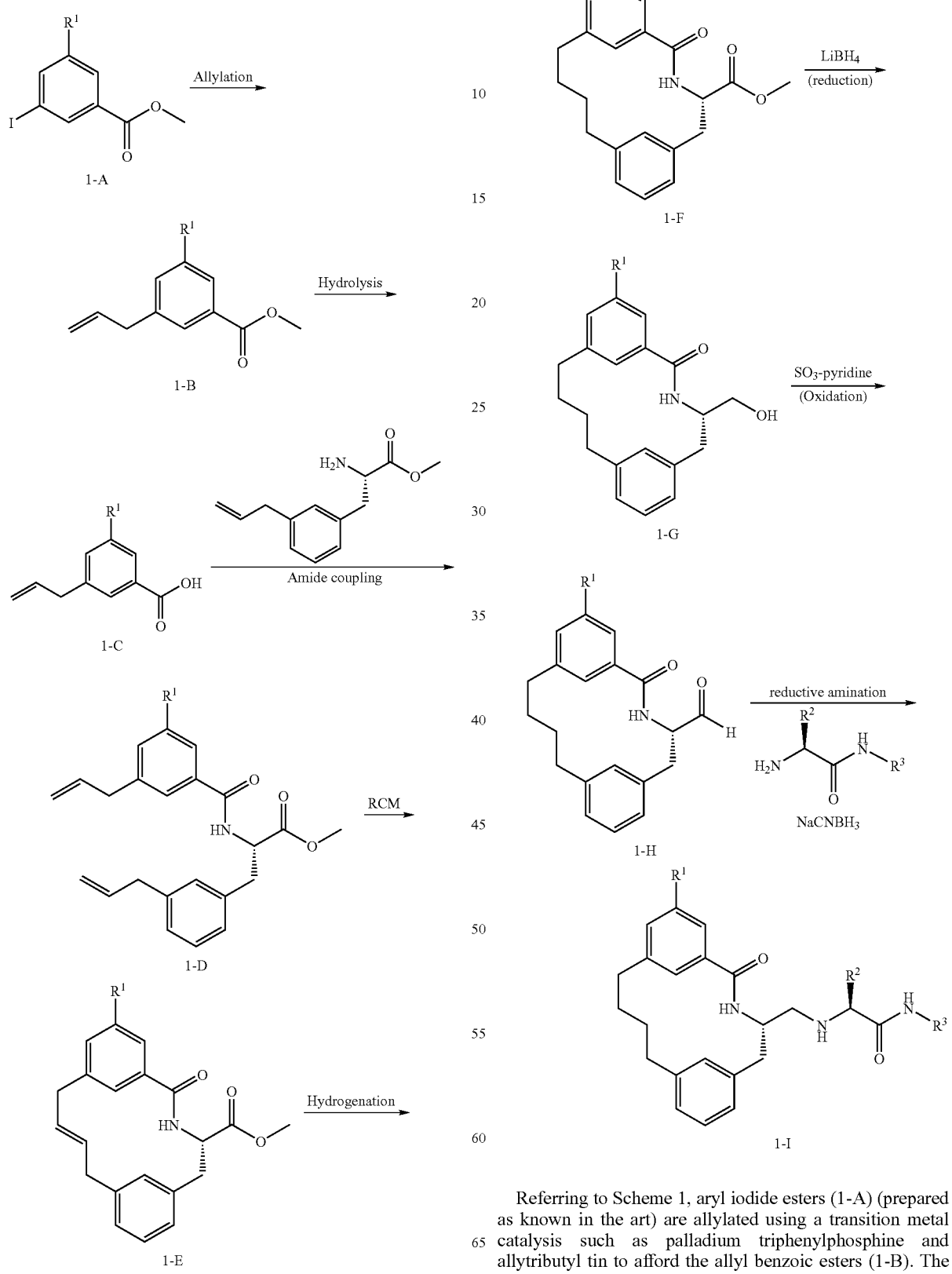

Referring to Scheme 1, aryl iodide esters (1-A) (prepared as known in the art) are allylated using a transition metal catalysis such as palladium triphenylphosphine and allytributyl tin to afford the allyl benzoic esters (1-B). The ester is hydrolyzed under basic conditions such as 2N NaOH in tetrahydrofuran/methanol. The resulting acid (1-C) is coupled to methyl-3-allyl-L-phenylalaninate hydrochloride in the presence of a coupling agent such as BOP reagent and an amine base to afford the amide diene (1-D). The diene is treated with a ring closing metathesis catalyst to afford the macrocyclic alkene (1-E). The resulting macrocyclic alkene is reduced under standard hydrogenation conditions to afford the saturated macrocycle (1-F). The ester is reduced to the corresponding alcohol (1-G) using a reducing agent such as lithium borohydride. The alcohol is subjected to standard oxidation conditions such as sulfur trioxide pyridine in the presence of triethylamine to afford the aldehyde (1-H). The resulting aldehyde is reductively aminated with the appropriate amine using a reducing agent such as sodium cyanoborohydride to provide the final compounds (1-I).

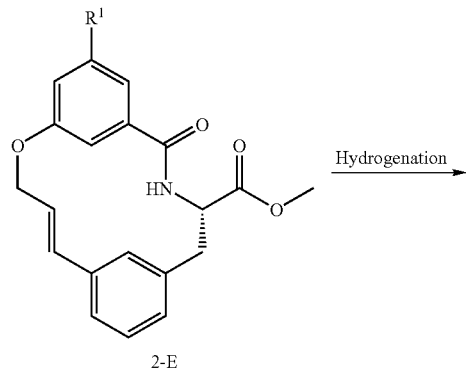

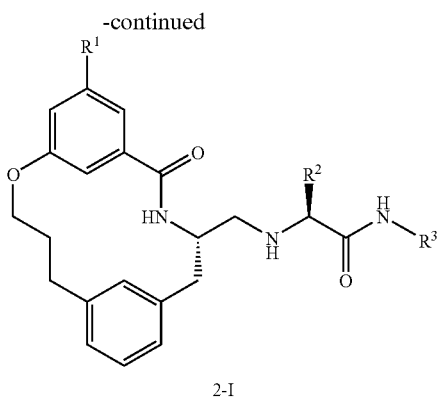

2-I

Referring to Scheme 2, phenol esters (2-A) (prepared as known in the art) are allylated using an allyl halide and a base such as potassium carbonate to provide the allyl ether benzoic ester (2-B). The ester is hydrolyzed under basic conditions such as 2N NaOH in tetrahydrofuran/methanol. The resulting acid (2-C) is coupled to methyl-3-allyl-L-phenylalaninate hydrochloride in the presence of a coupling agent such as BOP reagent and an amine base to afford the amide diene (2-D). The diene is treated with a ring closing metathesis catalyst to afford the macrocyclic alkene (2-E). The resulting macrocyclic alkene is reduced under standard hydrogenation conditions to afford the saturated macrocycle (2-F). The ester is reduced to the corresponding alcohol (2-G) using a reducing agent such as lithium borohydride. The alcohol is subjected to standard oxidation conditions such as sulfur trioxide pyridine in the presence of triethylamine to afford the aldehyde (2-H). The resulting aldehyde is reductively aminated with the appropriate amine using a reducing agent such as sodium cyanoborohydride to provide the final compounds (2-I).

The term "substantially pure" means that the isolated material is at least 90% pure, and preferably 95% pure, and even more preferably 99% pure as assayed by analytical techniques known in the art. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids.

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating, preventing the progression, ameliorating, controlling or reducing the risk of Alzheimer's disease, other diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment, prevention, control, amelioration, or reduction of risk of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with: anti-Alzheimer's agents, for example other beta-secretase inhibitors or gamma-secretase inhibitors, HMG-CoA reductase inhibitors; NSAID's including ibuprofen; vitamin E; anti-amyloid antibodies, including humanized monoclonal antibodies; CB-1 receptor antagonists or CB-1 receptor inverse agonists; antibiodies such as doxycycline and rifampin; N-methyl-D-aspartate (NMDA) receptor antagonists, such as memantine; cholinesterase inhibitors such as galantamine, rivastigmine, donepezil and tacrine; growth hormone secretagogues such as ibutamoren, ibutamoren mesylate, and capromorelin; histamine $H_3$ antagonists; AMPA antagonists; PDE-4 inhibitors; $GABA_A$ inverse agonists; neuronal nicotic agonists; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent or as soft gelatin capsules wherein the active ingredient is mixed with water or an oil medium.

Aqueous suspensions contain the active materials in admixture with excipients suitable for the manufacture of aqueous suspensions. Such excipients include suspending agents, and dispersing or wetting agents. The aqueous suspensions may also contain one or more preservatives, coloring agents, flavoring agents, and sweetening agents.

Oily suspensions may be formulated by suspending the active ingredient in a vegetable oil or in a mineral oil. The oily suspensions may also contain a thickening agent. Sweetening agents and flavoring agents may be added to provide a palatable oral preparation. These compositions may be preserved by the addition of an anti-oxidant.

Dispersible powders and granules suitable for preparation of an aqueous suspension by the addition of water provide the active ingredient in admixture with a dispersing or wetting agent, suspending agent and one or more preservatives. Additional excipients, for example sweetening, flavoring and coloring agents, may also be present.

The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, which may be formulated according to the known art, or may be administered in the form of suppositories for rectal administration of the drug.

The compounds of the present invention may also be adminsistered by inhalation, by way of inhalation devices known to those of ordinary skill in the art, or transdermally by way of a transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individuals body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

As used herein the term "treating" means any administration of a compound of the present invention and includes (1) inhibiting the disease in an animal that is experiencing or displaying the pathology or symptomatology of the disease (i.e., arresting further development of the pathology and/or symptomatology), or (2) ameliorating the disease in an animal that is experiencing or displaying the pathology or symptomatology of the disease (i.e., reversing the pathology and/or symptomatology). The term "controlling" includes preventing, treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person adminstering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples in the pharmacy arts of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person adminstering the drug to the patient. Such kits may be provided with all necessary materials and ingredients contained therein, or they may contain instructions for using or making materials or components that must be obtained independently by the patient or person administering the drug to the patient.

When treating, preventing, controlling, ameliorating, or reducing the risk of Alzheimer's disease or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. The total daily dosage is from about 1.0 milligrams to about 2000 milligrams, preferably from about 0.1 milligrams to about 20 milligrams per kilogram of body weight. In the case of a 70 kg adult human, the total daily dose will generally be from about 7 milligrams to about 1,400 milligrams. This dosage regimen may be adjusted to provide the optimal therapeutic response. The compounds may be administered on a regimen of 1 to 4 times per day, preferably once or twice per day. Generally, dosage levels of between 0.0001 to 10 mg/kg. of body weight daily are administered to the patient, e.g., humans and elderly humans. The dosage range will generally be about 0.5 mg to 1.0 g. per patient per day which may be administered in single or multiple doses. Preferably, the dosage range will be about 0.5 mg to 500 mg per patient per day; more preferably about 1 mg to 250 mg per patient per day; and even more preferably about 5 mg to 50 mg per patient per day.

Pharmaceutical compositions of the present invention may be provided in a solid dosage formulation preferably comprising about 0.5 mg to 500 mg active ingredient, more preferably comprising about 1 mg to 250 mg active ingredient. The pharmaceutical composition is preferably provided in a solid dosage formulation comprising about 1 mg, 5 mg, 10 mg, 25 mg, 30 mg, 50 mg, 60 mg, 100 mg, 150 mg, 200 mg or 250 mg active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

HPLC assay: A homogeneous end point HPLC assay is employed with the substrate (coumarin-CO-REVNFE-VEFR), which is cleaved by BACE 1 to release the N-terminal fragment attached with coumarin. The Km of the substrate is greater than 100 μM and can not be determined due to the limit of solubility of the substrate. A typical reaction contains approximately 2 nM enzyme, 1.0 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and the reaction is stopped by the addition of 25 μL of 1 M Tris-HCl, pH 8.0. The resulting reaction mixture was loaded on the HPLC and the product was separated from substrate with 5 min linear gradient. Under these conditions, less than 10% of substrate is processed by BACE 1. The enzyme used in these studies was soluble (transmembrane domain and cytoplasmic extension excluded) human protein produced in a baculovirus expression system. To measure the inhibitory potency for compounds, solutions of inhibitor in DMSO (12 concentrations of the inhibitors were prepared and the concentration rage was dependent on the potency predicted by FRET) were included in the reaction mixture (final DMSO concentration is 10%). All experiments were conducted at room temperature using the standard reaction conditions described above. To determine the $IC_{50}$ of the compound, four parameters equation is employed for curve fitting. The errors in reproducing the dissociation constants are typically less than two-fold.

In particular, the compounds of the following examples had activity in inhibiting the beta-secretase enzyme in the aforementioned assay, generally with an $IC_{50}$ from about 1 nM to 1 μM. Such a result is indicative of the intrinsic activity of the compounds in use as inhibitors the beta-secretase enzyme activity.

Several methods for preparing the compounds of this invention are illustrated in the following Schemes and Examples. Starting materials are made according to procedures known in the art or as illustrated herein. The following examples are provided so that the invention might be more fully understood. These examples are illustrative only and should not be construed as limiting the invention in any way. $^1$H NMR was obtained on a spectrometer running at 400 MHz.

EXAMPLE 1

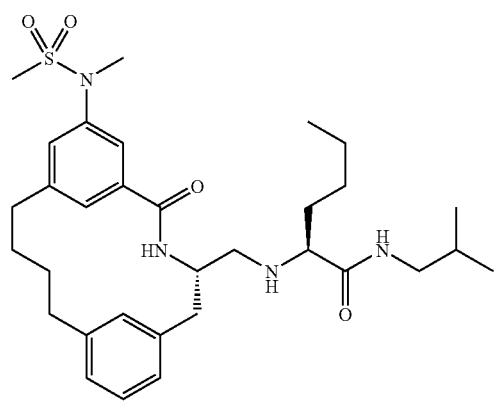

Step A: To 3-Nitrobenzoate (35.3 g, 195 mmol) in trifluoromethane sulfonic acid (100 mL) at 0° C. was added N-iodosuccinimide (43.8 g, 195 mmol) portionwise. The ice bath was removed and stirring was continued at ambient temperature for 48 hrs. The reaction mixture was cooled to 0° C. and quenched with water (500 mL). The mixture was extracted three times with EtOAc (250 mL) and the combined extracts were washed with a 10% NaHSO$_3$ solution. The organics were dried over MgSO$_4$, concentrated, and purified on silica gel (10% EtOAc in Hex) affording the intermediate. $^1$H NMR (CDCl$_3$) δ 8.81 (s, 1H), 8.73 (s, 1H), 8.68 (s, 1H), 4.00 (s, 3H).

Step B: Tin chloride (88.6 g, 392 mmol) in EtOH (50 mL) was refluxed and a 1:1 THF:EtOH (100 mL) solution of the nitrobenzoate from step A (24.1 g, 78.4 mmol) was added dropwise. The reaction mixture was refluxed for 30 minutes then cooled to 0° C. The solution was basified to pH 8-9 with aq. Na$_2$CO$_3$. The aqueous layer was extracted with EtOAc (3×700 mL). The combined organics were washed with saturated NaHCO$_3$ then brine. The organics were dried over Na$_2$SO$_4$ and concentrated affording the crude aniline. LCMS [M+H]=278.0.

Step C: To a 0° C. solution of the aniline from step B (21.7 g, 78.3 mmol) in 3:1 CH$_2$Cl$_2$:pyridine (75 mL) was added methanesulfonyl chloride (6.36 mL, 82.2 mmol). The ice bath was removed after 15 minutes and the reaction mixture was stirred overnight at room temperature. The reaction mixture was diluted with EtOAc (200 mL), washed 2×1N HCl, and dried over MgSO$_4$. The solvent was removed in vacuo and the residue was purified by silica gel chromatography (1:1 EtOAc/Hexanes) to provide he sulfonamide. LCMS [M$^+$] 355.8. $^1$H NMR (CDCl$_3$) δ 8.17 (s, 1H), 7.86 (s, 1H), 7.18 (s, 1H), 3.95 (s, 3H), 3.08 (s, 3H).

Step D: NaH (0.49 g, 12.30 mmol, 60% oil dispersion) was added to a solution of the sulfonamide from step C (3.12 g, 8.79 mmol), and methyl iodide (1.75 g, 12.3 mmol) in DMF (20 mL). The reaction was stirred at 50° C. for 2 hours after which the reaction was quenched with saturated NH$_4$Cl and extracted with EtOAc (3×100 mL). The combined organics were washed with water (2×100 mL), brine (1×50 mL) and dried of MgSO$_4$. The solvent was removed in vacuo and the residue was purified by silica gel chromatography (25% EtOAc/Hexanes) to provide the N-methlysulfonamide. LCMS [M$^+$]: 369.9. $^1$H NMR (CDCl$_3$) δ 8.29 (s, 1H), 7.96 (s, 2H), 3.93 (s, 3H), 3.34 (s, 3H), 2.88 (s, 3H).

Step E: A DMF solution (20 mL) of iodide from step D (3.15 g, 8.54 mmol) and allyltributyl stannane (3.39 g, 10.24 mmol) was degassed with a stream of argon for 15 minutes. To the degassed solution was added Pd(PPh$_3$)$_4$ (0.99 g, 0.85 mmol) after which the reaction mixture was heated to 80° C. for 2 h. The solution was cooled, diluted with H$_2$O (250 mL), and extracted with EtOAc (3×100 mL).). The combined organic layers were washed with water (2×100 mL), brine (1×50 mL), and dried of MgSO$_4$. The solvent was removed in vacuo and the residue was purified by silica gel chromatography (40% EtOAc/Hexanes) to provide the allylated product.
LCMS [M+H]: 284.1. $^1$H NMR (CDCl$_3$) δ 7.84 (s, 1H), 7.82 (s, 1H), 7.47 (s, 1H), 5.97 (m, 1H), 5.14 (m, 2H), 3.93 (s, 3H), 3.46 (d, J=6.7 Hz, 2H), 3.36 (s, 3H), 2.87 (s, 3H).

Step F: To the ester from step E (1.79 g, 6.34 mmol) in 40 mL THF:MeOH (1:1) was added 2N NaOH (9.51 mL, 19.0 mmol). The solution was heated to 50° C. for 1 h. The reaction mixture was concentrated, acidified with 1N HCl (50 mL), and extracted with EtOAc (3×50mL). The combined extracts were dried over MgSO$_4$, filtered, and concentrated in vacuo to yield the desired carboxylic acid. LCMS [M+H]=270.2.

Step G: A solution containing the carboxylic acid from step F (1.38 g, 5.13 mmol), m-allyl tyrosine methyl ester HCl (see Tilley et al., *J Med Chem* 1991 (34) (3) 1125-1136 for analogous preparation) (1.31 g, 5.13 mmol) BOP reagent (2.27 g, 5.39 mmol), and diisopropyl ethylamine (2.68 mL, 15.39 mmol) was stirred at rt for 1 h in 100 mL of DCM. The solvent was evaporated and the residue was purified by silica gel chromatography (1:1 EtOAc/Hexanes) to afford the desired amide as a light yellow oil. LCMS [M+H]=471.1. $^1$H NMR (CDCl$_3$) δ 7.60 (s, 1H), 7.40 (s, 1H), 7.38 (s, 1H), 7.23 (t, J=7.6 Hz, 1H), 7.10 (d, J=7.3 Hz, 1H), 6.98 (d, J=11 Hz, 1H), 6.96 (s, 1H), 6.55 (d, J=7.2 Hz, 1H), 5.98-5.86 (m, 2H), 5.15-5.01 (m, 4H), 3.77 (s, 3H), 3.42 (d, J=6.4 Hz, 2H), 3.34 (d, J=7.0 Hz, 2H), 3.33 (s, 3H), 3.23 (dd, J=8.3, 5.8 Hz, 2H), 2.84 (s, 3H).

Step H: 2.17 g (4.61 mmol) of the diene from step G was dissolved in DCM (2 L) and degassed with a steam of argon for 15 min. Tricyclohexylphosphine[1,3-bis(2,4,6-trimethylphenyl)4,5-dihydroimidazo[-2-ylidine][benzylidine]ruthenium(IV)dichloride (0.42 g, 0.49 mmol) was added and the reaction mixture was heated to 50° C. for 30 min. The reaction was cooled, DMSO (1 mL) was added and the reaction was stirred at rt for 12 h. The solvent was evaporated and the residue was purified by silica gel chromatography (80% EtOAc/Hexanes) to provide the desired macrocycle as a single geometric isomer. LCMS [M+H]=443.0. $^1$H NMR (CDCl$_3$) δ 7.64 (s, 2H), 7.47 (s, 1H), 7.29 (t, J=7.5 Hz, 1H), 7.20 (s, 1H), 7.18 (d, J=9.3 Hz, 1H), 6.96 (d, J=7.5 Hz, 1H), 6.40 (d, J=9.0 Hz, 1H), 5.73 (m, 2H), 5.09 (m, 1H), 3.80 (s, 3H), 3.52-3.23 (m, 5H), 3.32 (s, 3H), 3.04 (dd, J=13, 5.4 Hz, 1H), 2.83 (s, 3H).

Step I: A solution of the macrocyclic alkene from step H in 50 mL of MeOH was treated with a catalytic amount of 10% Pd/C and stirred at rt under a hydrogen atmosphere for 2 h. The reaction was filtered through a pad of celite and the solvent was removed in vacuo to provide the reduced macrocycle as a white foam. LCMS [M+H] =445.26. $^1$H NMR (CDCl$_3$) δ 7.59 (s, 1H), 7.38 (s, 1H), 7.28 (t, J=7.6 Hz, 1H), 7.16 (d, J=7.5 Hz, 1H), 7.05 (s, 1H), 6.96 (d, J=7.5 Hz, 1H), 6.83 (s, 1H), 6.19 (d, J=8.0 Hz, 1H), 4.99 (dd, J=12, 5.7 Hz, 1H), 3.86 (s, 3H), 3.31 (s, 3H), 3.29 (m, 1H), 3.18 (dd, J=14, 6.0 Hz, 1H), 2.84 (m, 2H), 2.83 (s, 3H), 2.72 (dd, J=18, 6.5 Hz, 1H), 2.59 (t, J=11 Hz, 1H), 1.81-1.58 (m, 4H).

Step J: A solution containing the reduced alkene from step I (1.05 g, 2.36 mmol) in THF (30 mL) was treated with LiBH$_4$ (2.0M THF solution, 3.54 mL, 7.08 mmol). The reaction mixture was heated to 50° C. for 1 h. The reaction was quenched by the addition of cold methanol. The solvent was removed in vacuo and the residue was purified by silica gel chromatography (5% methanol/chlorform) to provide the desired alcohol as a white foam. LCMS [M+H]=417.1. $^1$H NMR (CDCl$_3$) δ 7.54 (s, 1H), 7.37-7.33 (m, 2H), 7.19-7.16 (m, 2H), 7.08 (s, 1H), 6.51 (s, 1H), 6.18 (d, J=4.0 Hz, 1H), 4.03 (m, 1H), 3.90 (dd, J=11, 2.9 Hz, 1H), 3.80 (dd, J=11, 7.3 Hz, 1H), 3.29 (s, 3H), 3.12 (dd, J=13, 4.9 Hz, 1H), 2.89 (dd, J=13, 4.9 Hz, 1H), 2.83 (s, 3H), 2.83 (m, buried, 1H), 2.75-2.66 (m, 2H), 2.59-2.53 (m, 1H)m 1.83-1.64 (m, 4H).

Step K: A solution containing the alcohol from step J (0.143 g, 0.343 mmol) in 4 mL DMSO:DCM (3:1) was treated with triethylamine (0.17 g, 1.71 mmol) then SO$_3$-pyridine complex (0.21 g, 1.37 mmol). The reaction mixture was stirred at rt for 1 h. The solution was diluted with H$_2$O (25 mL) and extracted with EtOAc (3×25 mL). The combined organic layers were washed with 1N HCl (2×50 mL) and brine (1×50 mL) then dried over MgSO$_4$. The solution was filtered and concentrated in vacuo to afford the desired aldehyde. LCMS [M+H]=415.1.

Step L: A solution containing the aldehyde from step K (0.040 g, 0.096 mmol) and N-isobutyl-L-norleucinamide HCl (0.064 g, 0.289 mmol) in 5 mL MeOH was treated with NaCNBH$_3$ (0.018 g, 0.289 mmol) and stirred at rt for 12 h. The solvent was evaporated and the residue was purified by reverse phase HPLC to afford the title compound. LCMS [M+H]=585.2. $^1$H NMR (CD$_3$OD) δ 7.47 (s, 1H), 7.35 (s, 1H), 7.30 (t, J=7.3, 1H), 7.30 (s, 1H), 7.20 (d, J=8.1 Hz, 1H), 7.14 (d, J=7.2 Hz, 1H), 6.60 (s, 1H), 4.29 (m, 1H), 0.391 (t, J=6.5 Hz, 1H), 3.41-3.27 (m, 2H), 3.27 (s, 3H), 3.25 (m, 2H), 3.04 (dd, J=13, 6.9 Hz, 1H), 2.89 (m, 1H), 2.87 (s, 3H), 2.75 (m, 2H), 2.52 (m, 1H), 1.93-1.64 (m, 9H), 1.43 (m, 3H), 0.96 (d, J=6.7 Hz, 6H), 0.96 (t, buried, 3H).

The following compounds were prepared in a manner similar to the compounds of the foregoing schemes and examples using appropriate starting materials and reagents.

| Ex | Structure |
|---|---|
| 2 | 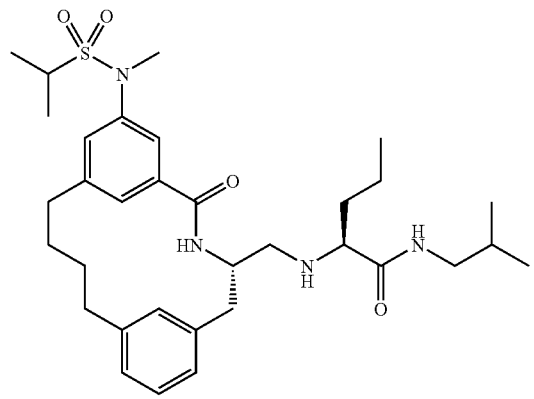 |
| 3 | 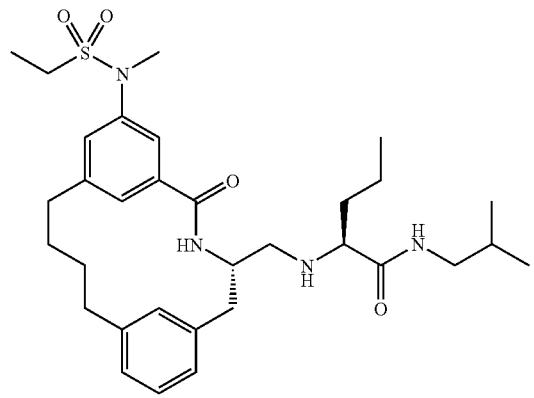 |
| 4 | 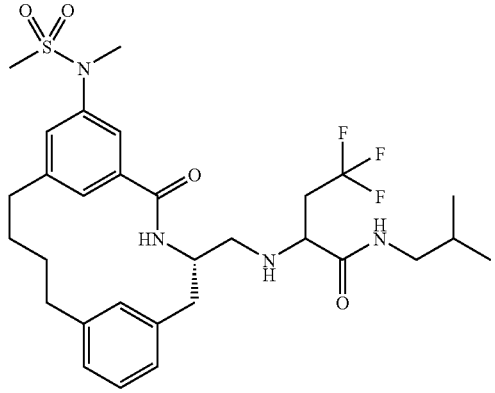 |
| 5 | 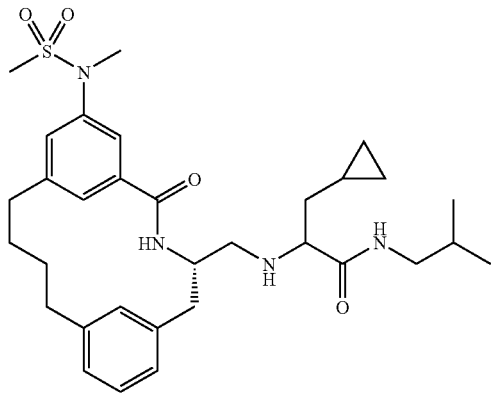 |
| 6 | 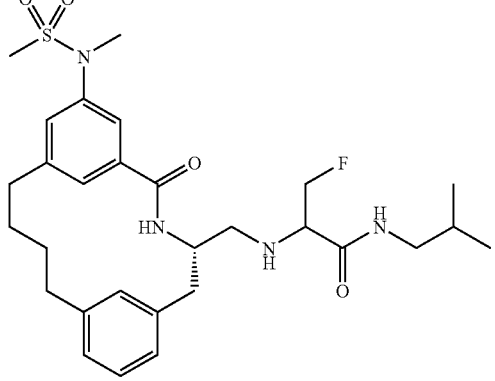 |
| 7 | 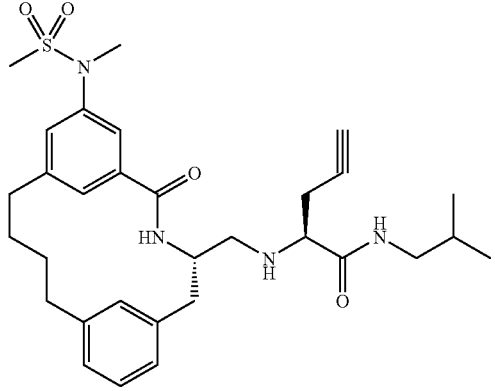 |

-continued
| Ex | Structure |
|---|---|
| 8 | 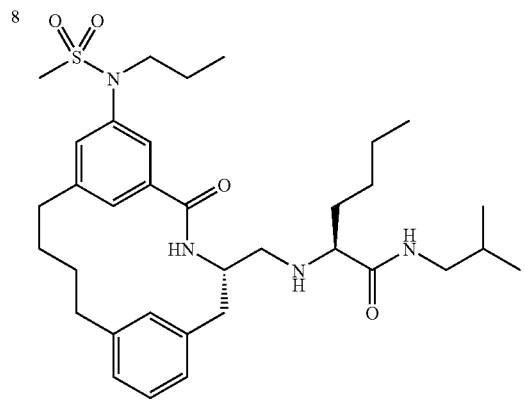 |
| 9 | 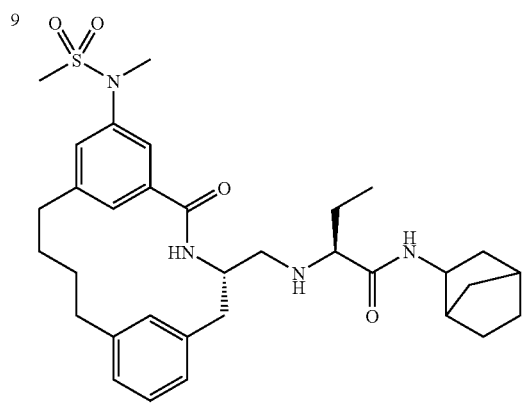 |
| 10 | 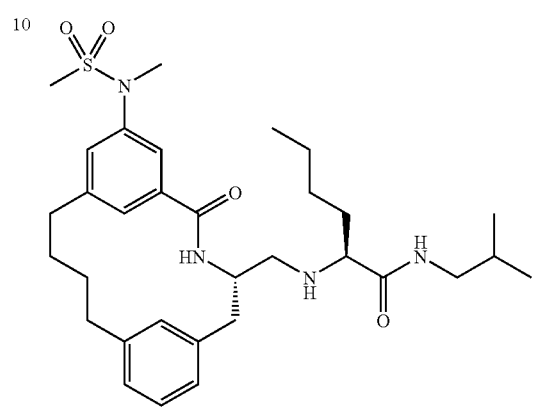 |
-continued
| Ex | Structure |
|---|---|
| 11 | 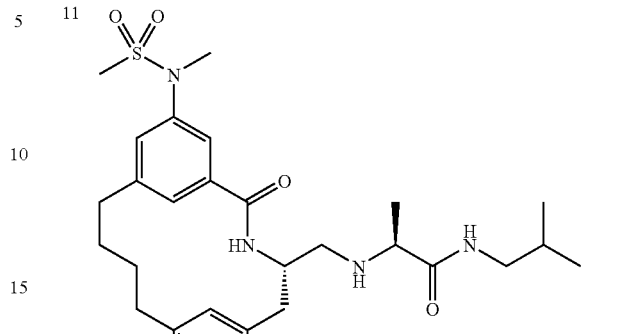 |
| 12 | 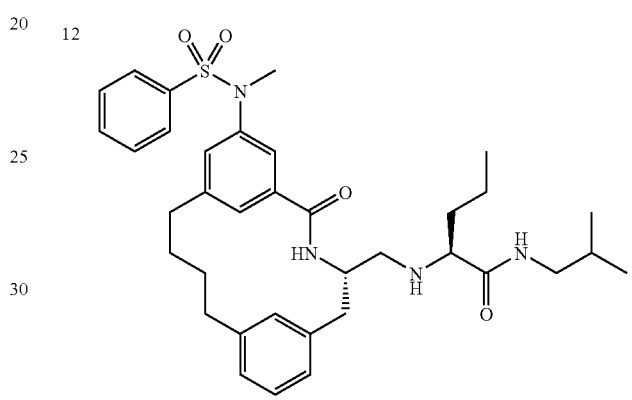 |
| 13 | 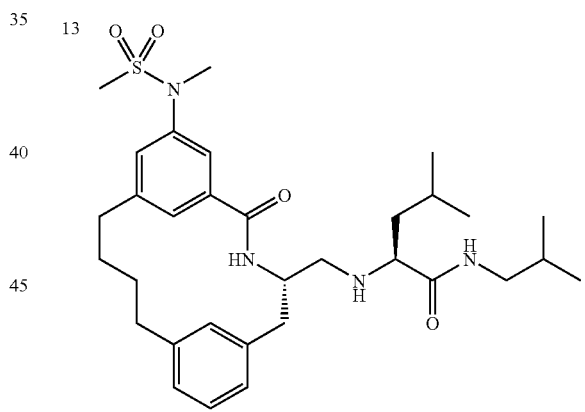 |
| 14 | 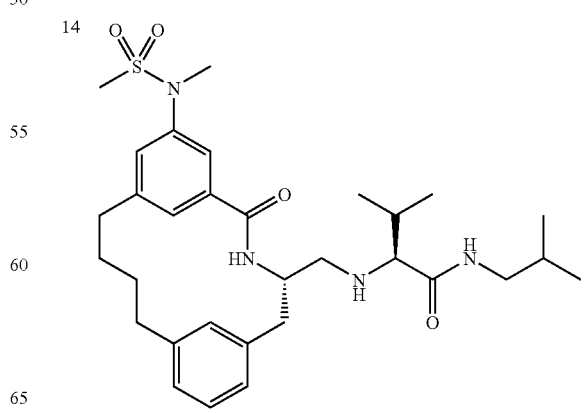 |

| Ex | Structure |
|---|---|
| 15 | 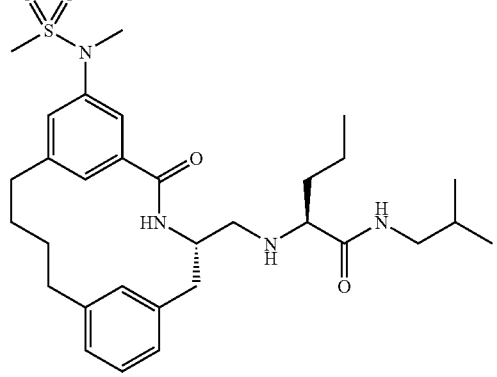 |
| 16 | 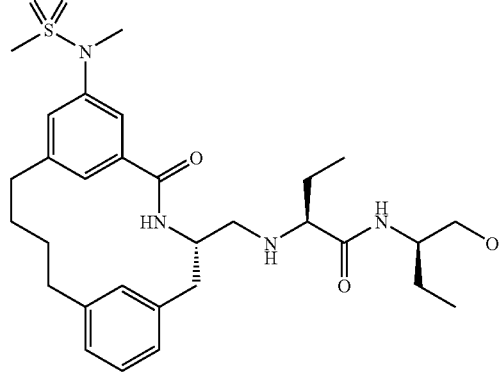 |
| 17 | 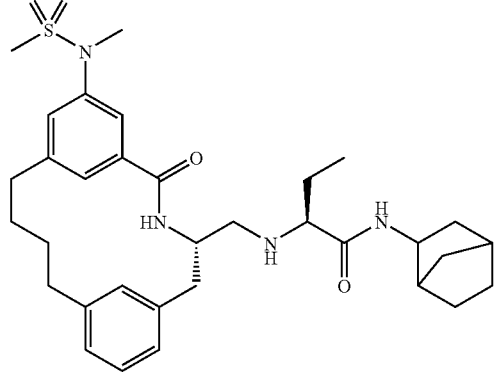 |
| 18 | 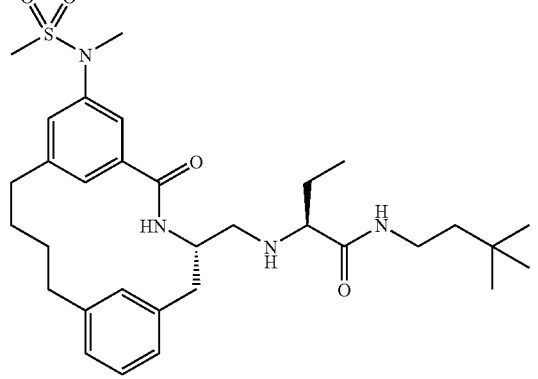 |
| 19 | 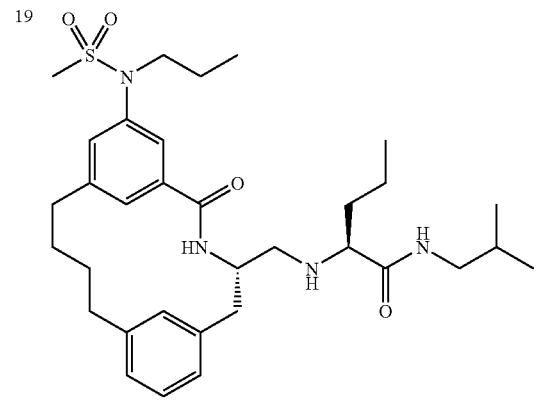 |
| 20 | 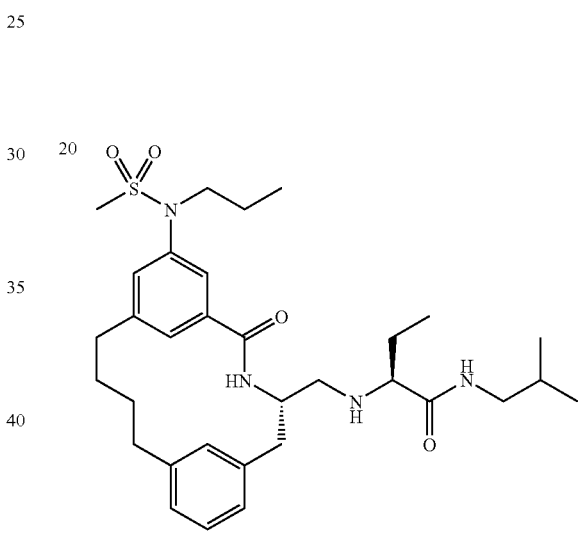 |
| 21 | 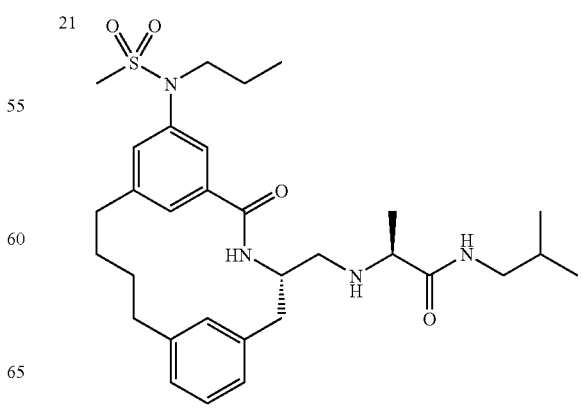 |

-continued
| Ex | Structure |
|---|---|
| 22 | 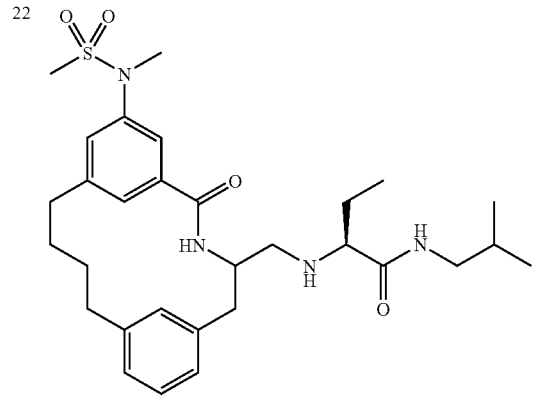 |
| 23 | 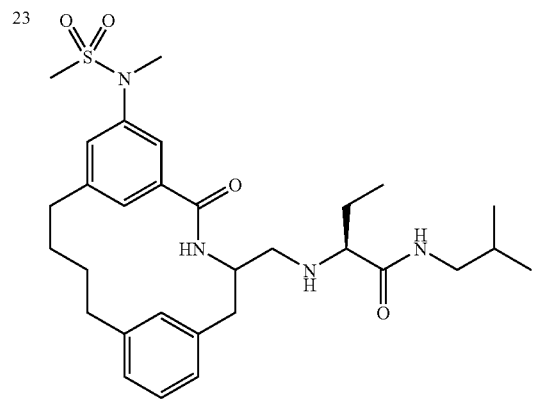 |
| 24 | 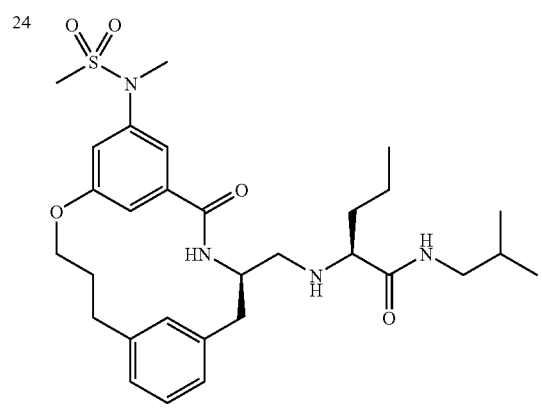 |
| 25 | 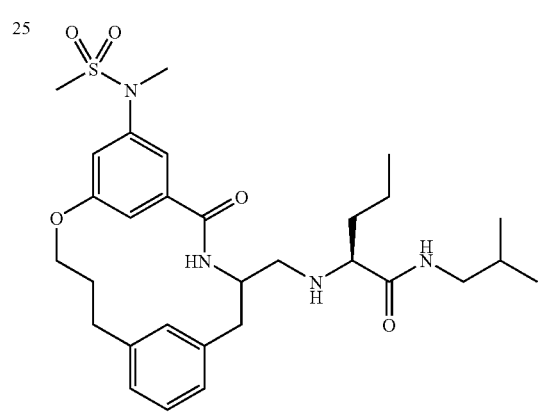 |
-continued
| Ex | Structure |
|---|---|
| 26 | 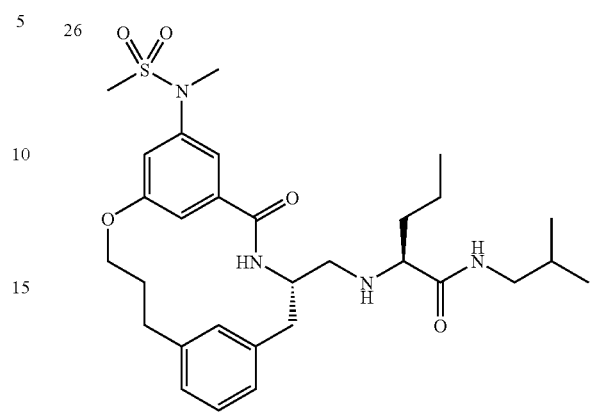 |
| 27 | 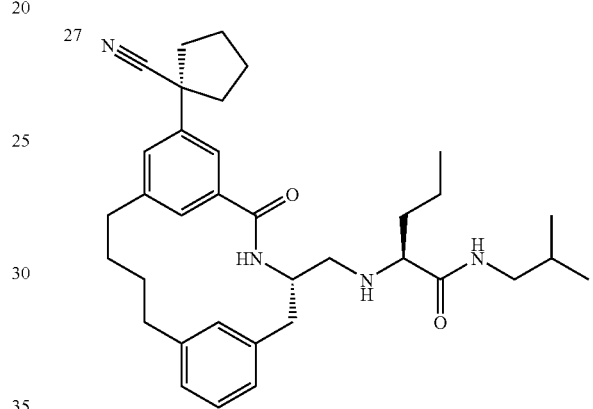 |
| 28 | 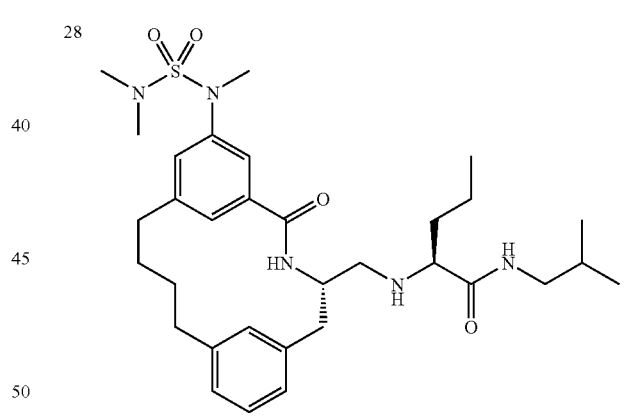 |
| 29 | 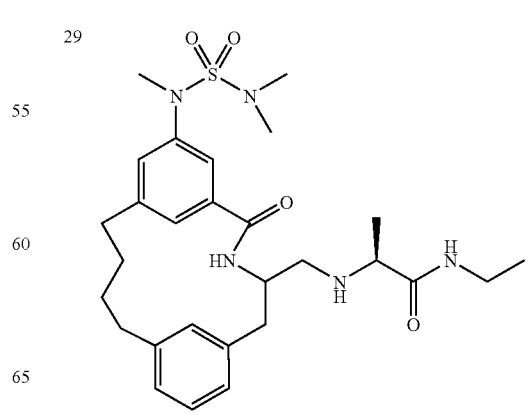 |

-continued
| Ex | Structure |
|---|---|
| 30 | 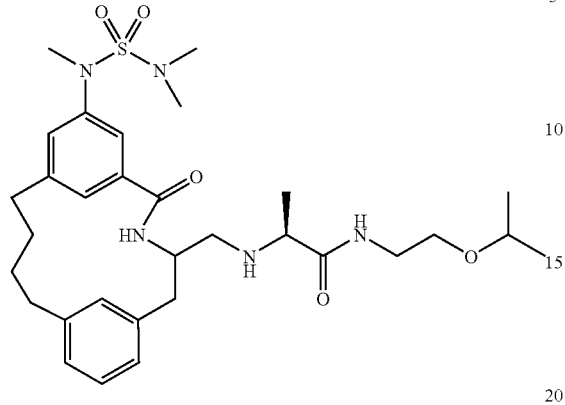 |
| 31 | 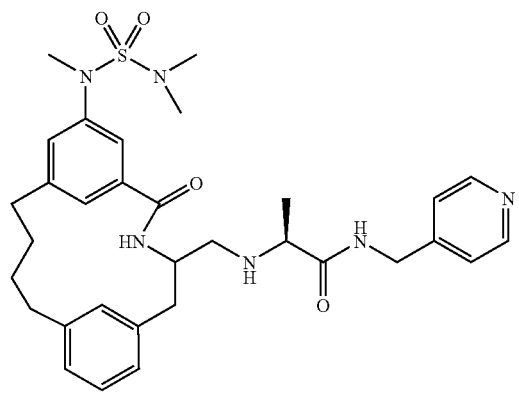 |
| 32 | 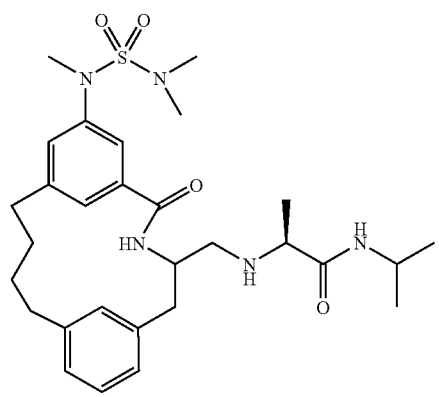 |
| 33 | 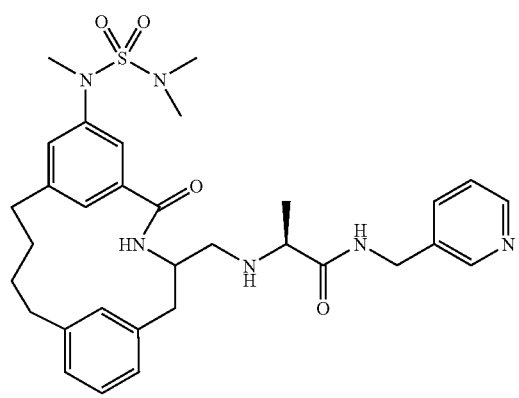 |
-continued
| Ex | Structure |
|---|---|
| 34 | 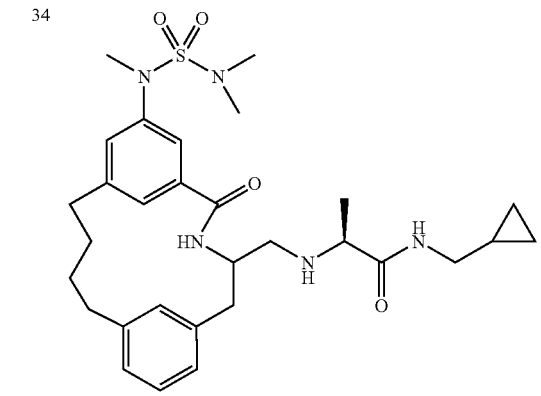 |
| 35 | 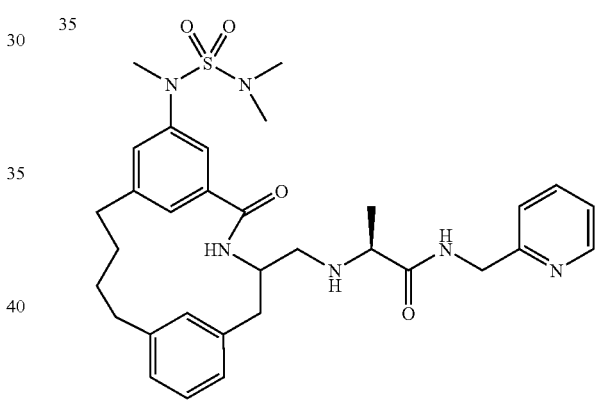 |
| 36 | 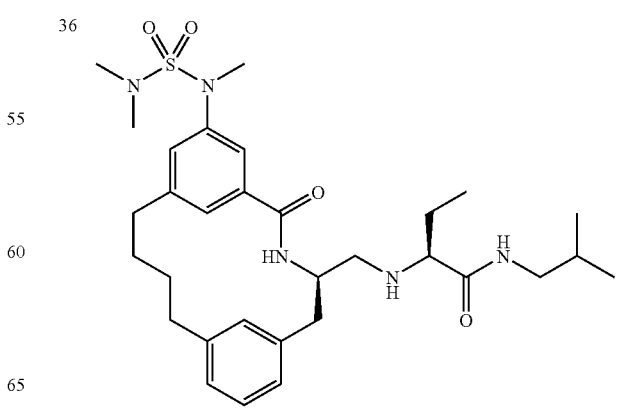 |

-continued

| Ex | Structure |
|---|---|
| 37 | 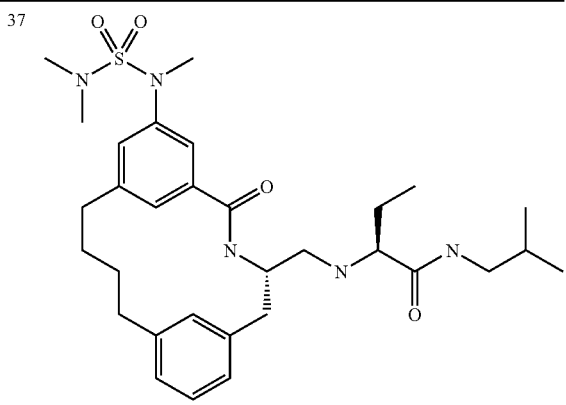 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of the formula I:

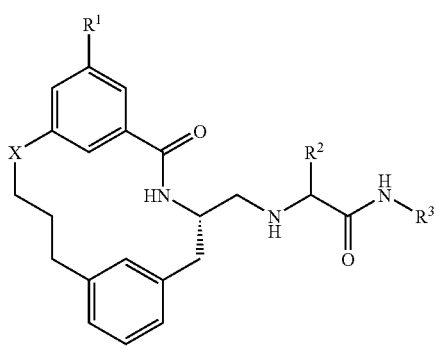

wherein:
$R^1$ is
$R^4$—$S(O)_p N(R^5)$—,
  wherein $R^4$ is independently selected from the group consisting of:
  (a) —$C_{1-8}$alkyl, which is unsubstituted or substituted with 1-6 fluoro,
  (b) —$NR^5R^6$,
  (c) phenyl, and
  (d) benzyl,
  wherein $R^5$ and $R^6$ are independently selected from the group consisting of:
  (a) hydrogen,
  (b) —$C_{1-6}$alkyl, which is unsubstituted or substituted with 1-6 fluoro,
  (c) phenyl, and
  (d) benzyl,
  and wherein p is independently 0, 1, or 2;

$R^2$ is selected from the group consisting of:
(1) hydrogen,
(2) —$C_{1-6}$alkyl, —$C_{2-6}$alkenyl, —$C_{2-6}$alkynyl, or —$C_{3-8}$cycloalkyl which is unsubstituted or substituted with 1-7 substituents where the substituents are independently selected from:
  (a) halo,
  (b) hydroxy,
  (c) —O—$C_{1-6}$alkyl,
  (d) —$C_{3-6}$cycloalkyl,
  (e) —$S(O)_p$—$C_{1-6}$alkyl,
  (f) —CN,
  (g) —$CO_2H$,
  (h) —$CO_2$—$C_{1-6}$alkyl,
  (i) —CO—$NR^5R^6$,
  (j) phenyl, which is unsubstituted or substituted with 1-5 substituents where the substituents are independently selected from:
    (i) —$C_{1-6}$alkyl,
    (ii) —CN,
    (iii) halo,
    (iv) —$CF_3$,
    (v) —O—$R^5$, and
    (vi) —$CO_2R^5$,
(3) phenyl which is unsubstituted or substituted with 1-5 substituents where the substituents are independently selected from:
  (a) —$C_{1-6}$alkyl,
  (b) —CN,
  (c) halo,
  (d) —$CF_3$,
  (e) —O—$R^5$, and
  (f) —$CO_2R^5$;

$R^3$ is selected from the group consisting of:
(1) hydrogen,
(2) —$C_{1-6}$alkyl, —$C_{2-6}$alkenyl, —$C_{2-6}$alkynyl, or —$C_{3-8}$cycloalkyl which is unsubstituted or substituted with 1-7 substituents where the substituents are independently selected from:
  (a) halo,
  (b) hydroxy,
  (c) —O—$C_{1-6}$alkyl,
  (d) —$C_{3-6}$cycloalkyl,
  (e) phenyl or pyridyl, which is unsubstituted or substituted with 1-5 substituents where the substituents are independently selected from:
    (i) —$C_{1-6}$alkyl,
    (ii) —CN,
    (iii) halo,
    (iv) —$CF_3$,
    (v) —O—$R^5$, and
    (vi) —$CO_2R^5$,
  (f) —$S(O)_p N(R^5)$—$C_{1-6}$alkyl, and
  (g) —$S(O)_p N(R^5)$-phenyl,
(3) phenyl which is unsubstituted or substituted with 1-5 substituents where the substituents are independently selected from:
  (a) —$C_{1-6}$alkyl,
  (b) —CN,
  (c) halo,
  (d) —$CF_3$,
  (e) —O—$R^5$, and
  (f) —$CO_2R^5$;

X is selected from the group consisting of:
(1) —$CH_2$—, and
(2) —O—;
or a pharmaceutically acceptable salt thereof.

2. The compound of claim 1 of the formula II:

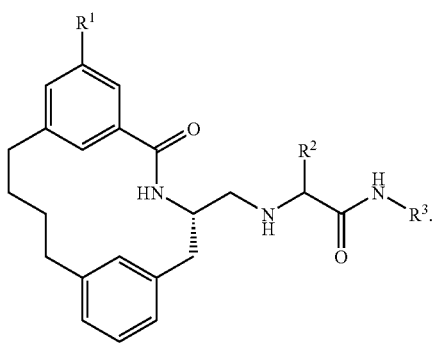

II

3. The compound of claim 2 wherein:
R¹ is selected from:
(1) $CH_3-S(O)_2N(CH_3)-$;
(2) $CH_3CH_2-S(O)_2N(CH_3)-$;
(3) $(CH_3)_2CH-S(O)_2N(CH_3)-$;
(4) phenyl-$S(O)_2N(CH_3)-$; and
(5) $(CH_3)_2N-S(O)_2N(CH_3)-$;
R² is $-C_{1-6}$alkyl, unsubstituted or substituted with cyclopropyl or halo;
R³ is $-C_{1-6}$alkyl or $-C_{3-8}$cycloalkyl; and
X is $-CH_2-$ or $-O-$;
or a pharmaceutically acceptable salt thereof.

4. The compound of claim 1 of the formula III:

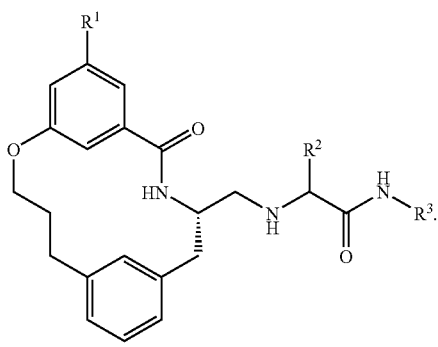

III

5. The compound of claim 1 wherein:
R¹ is selected from:
(1) $CH_3-S(O)_2N(CH_3)-$;
(2) $CH_3CH_2-S(O)_2N(CH_3)-$;
(3) $(CH_3)_2CH-S(O)_2N(CH_3)-$;
(4) phenyl-$S(O)_2N(CH_3)-$; and
(5) $(CH_3)_2N-S(O)_2N(CH_3)-$;
R² is $-C_{1-6}$alkyl, unsubstituted or substituted with cyclopropyl or halo;
R³ is $-C_{1-6}$alkyl or $-C_{3-8}$cycloalkyl; and
X is $-CH_2-$ or $-O-$;
or a pharmaceutically acceptable salt thereof.

6. The compound of claim 1 wherein:
R¹ is $R^4-S(O)_2N(R^5)-$,
wherein R⁴ is independently selected from the group consisting of:
(a) $-C_{1-6}$alkyl, which is unsubstituted or substituted with 1-6 fluoro,
(b) phenyl, and
(c) benzyl,
and wherein R⁵ is independently selected from the group consisting of:
(a) hydrogen,
(b) $-C_{1-6}$alkyl, which is unsubstituted or substituted with 1-6 fluoro,
(c) phenyl, and
(d) benzyl.

7. The compound of claim 6 wherein R¹ is selected from:
(1) $CH_3-S(O)_2N(CH_3)-$;
(2) $CH_3CH_2-S(O)_2N(CH_3)-$;
(3) $(CH_3)_2CH-S(O)_2N(CH_3)-$; and
(4) phenyl-$S(O)_2N(CH_3)-$;
(5) $(CH_3)_2N-S(O)_2N(CH_3)-$.

8. The compound of claim 7 wherein R¹ is $CH_3-S(O)_2N(CH_3)-$.

9. The compound of claim 1 wherein R² is $-C_{1-6}$alkyl, unsubstituted or substituted with cyclopropyl or halo.

10. The compound of claim 9 wherein R² is selected from:
(1) $CH_3-$;
(2) $CH_3CH_2-$;
(3) $(CH_3)_2CH-$;
(4) $CH_3CH_2CH_2-$;
(5) $(CH_3)_2CHCH_2-$;
(6) $CH_3CH_2CH_2CH_2-$;
(7) $CH_3CH_2CH_2CH_2CH_2-$;
(8) cyclopropyl-$CH_2-$;
(9) $CF_3CH_2-$; and
(10) $CH_2FCH_2-$.

11. The compound of claim 1 wherein R³ is $-C_{1-6}$alkyl or $-C_{3-8}$cycloalkyl.

12. The compound of claim 11 wherein R³ is selected from:
(1) $CH_3-$;
(2) $CH_3CH_2-$;
(3) $(CH_3)_2CH-$;
(4) $CH_3CH_2CH_2-$;
(5) $(CH_3)_2CHCH_2-$;
(6) $CH_3CH_2CH_2CH_2-$;
(7) $CH_3CH_2CH_2CH_2CH_2-$; and
(8) bicyclo[2.2.1]heptyl-.

13. The compound of claim 12 wherein R³ is $(CH_3)_2CHCH_2-$.

14. A compound of claim 1 which is selected from the group consisting of:

| Ex | Structure |
|---|---|
| 2 | 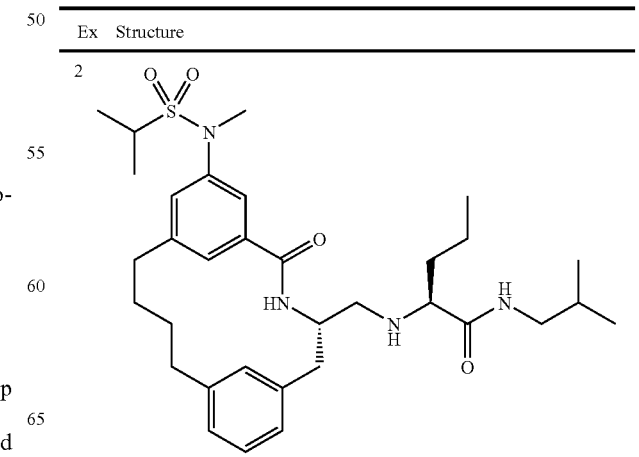 |

| Ex | Structure |
|---|---|
| 3 | 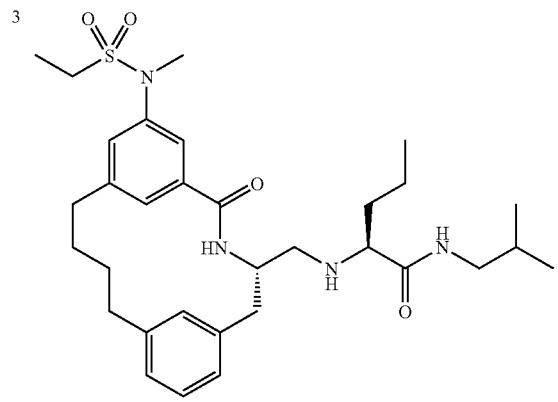 |
| 4 | 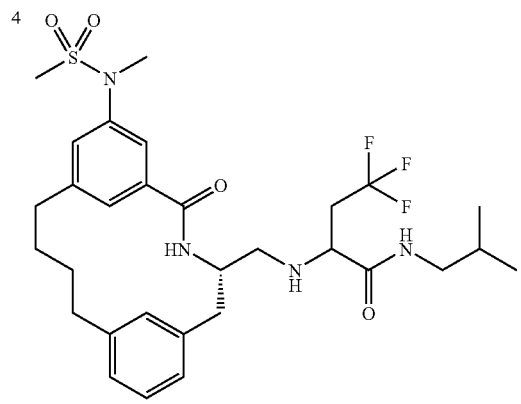 |
| 5 | 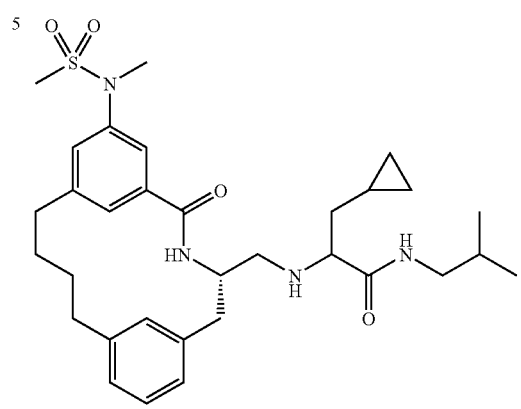 |
| 6 | 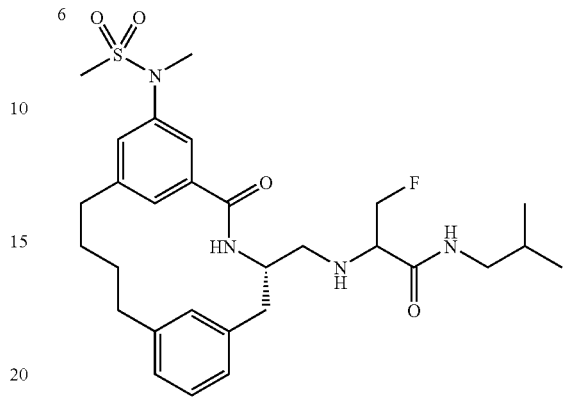 |
| 7 | 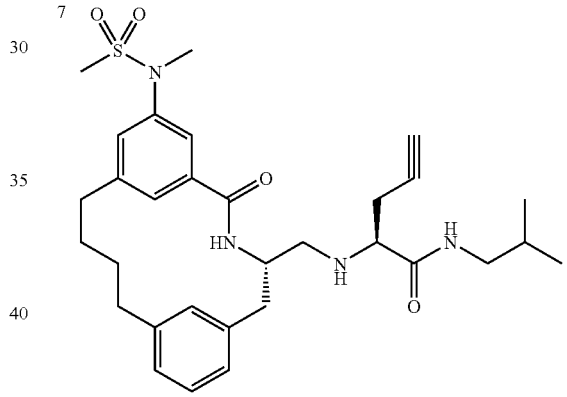 |
| 8 | 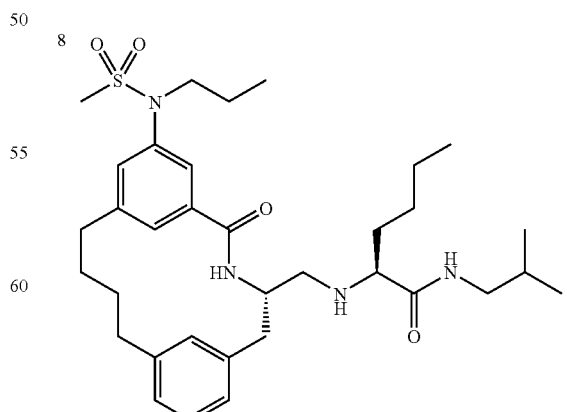 |

-continued
| Ex | Structure |
|---|---|
| 9 | 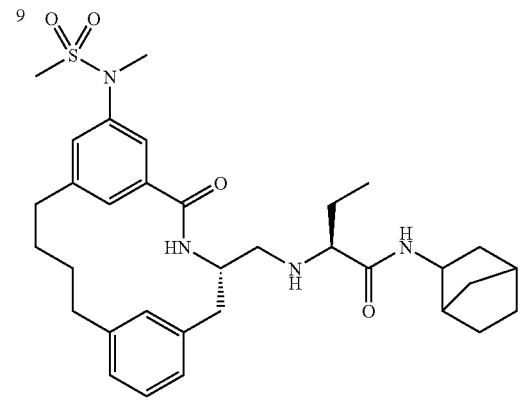 |
| 10 | 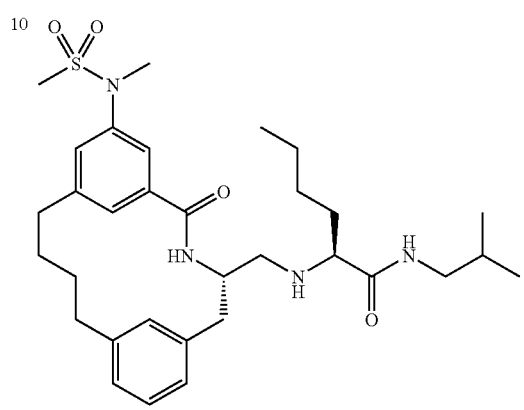 |
| 11 | 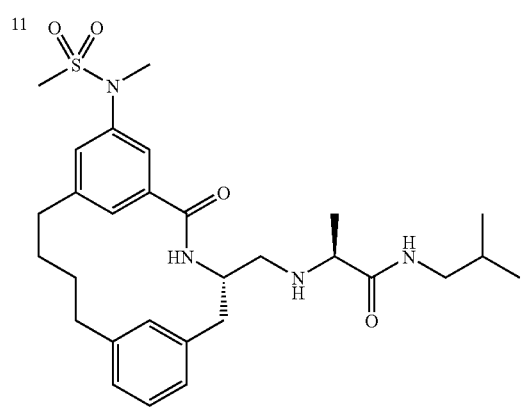 |
| 12 | 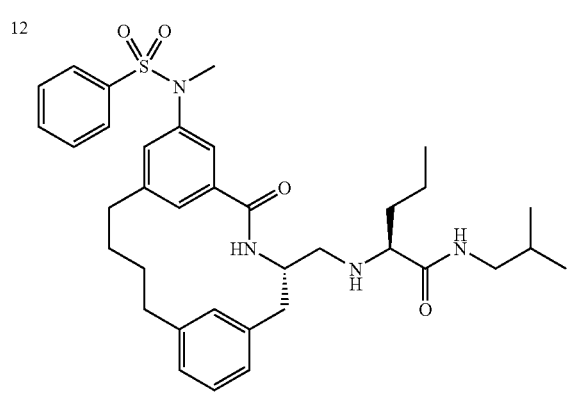 |
-continued
| Ex | Structure |
|---|---|
| 13 | 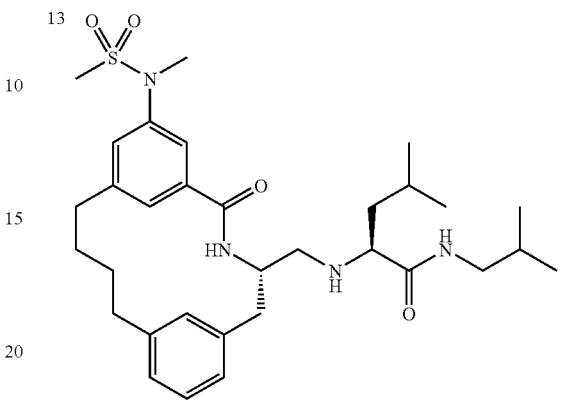 |
| 14 | 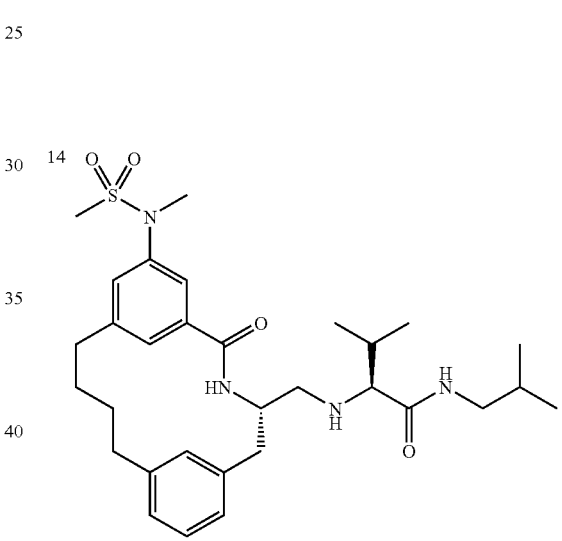 |
| 15 | 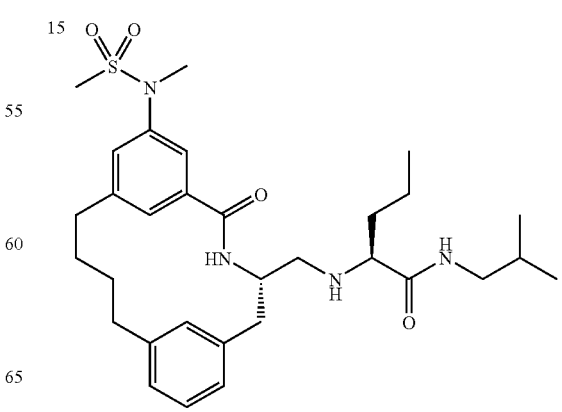 |

| Ex | Structure |
|---|---|
| 16 | 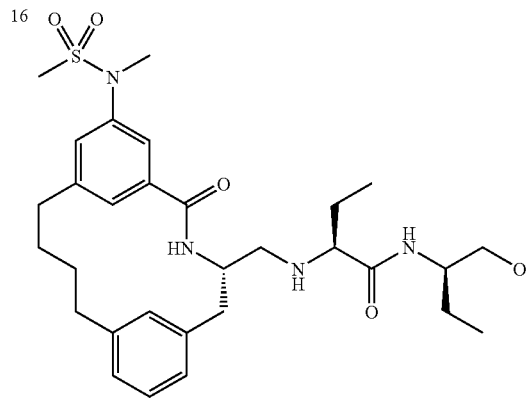 |
| 17 | 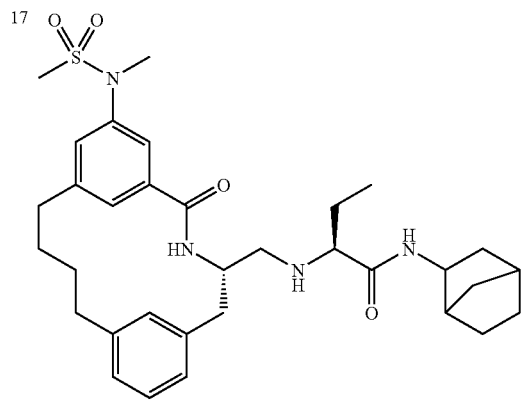 |
| 18 | 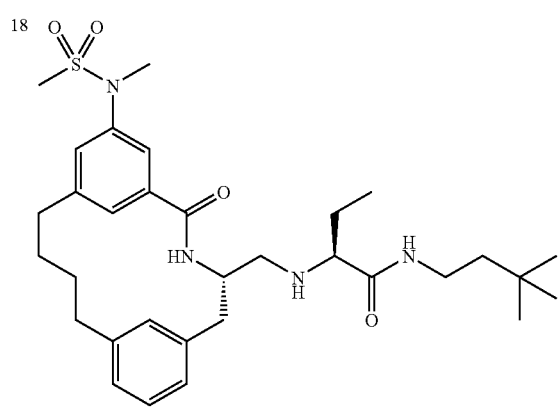 |
| Ex | Structure |
|---|---|
| 19 | 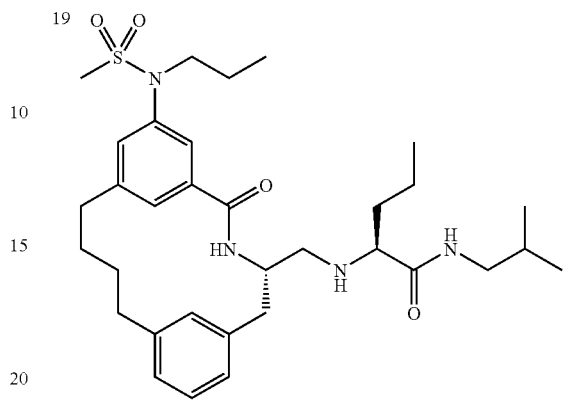 |
| 20 | 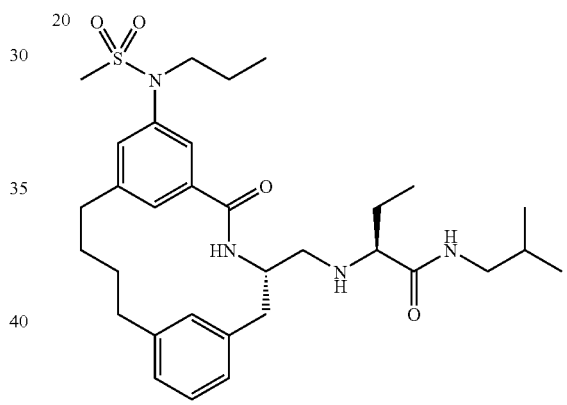 |
| 21 | 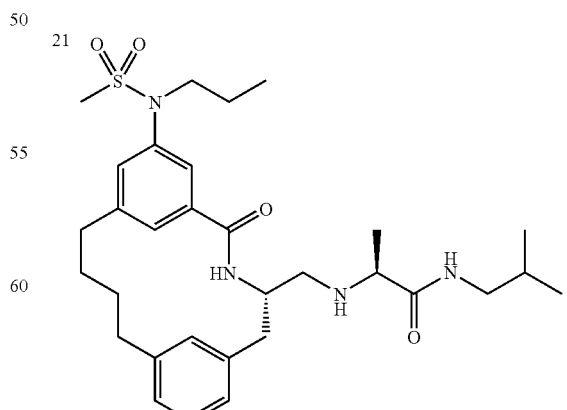 |

| Ex | Structure |
|---|---|
| 22 | 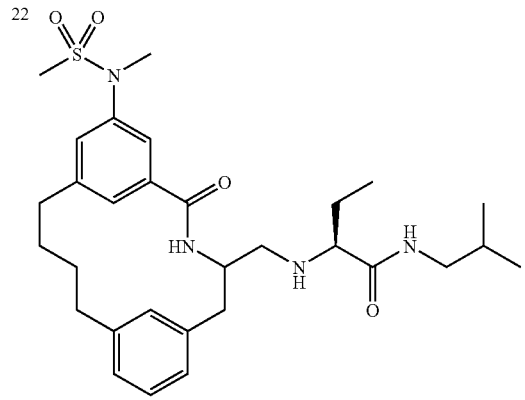 |
| 23 | 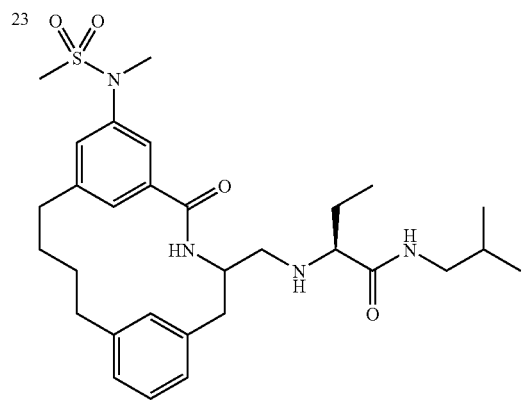 |
| 24 | 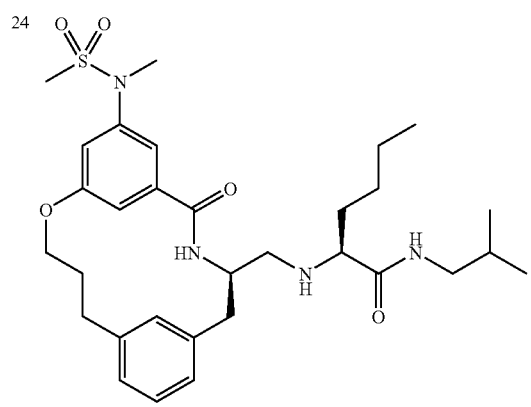 |
| Ex | Structure |
|---|---|
| 25 | 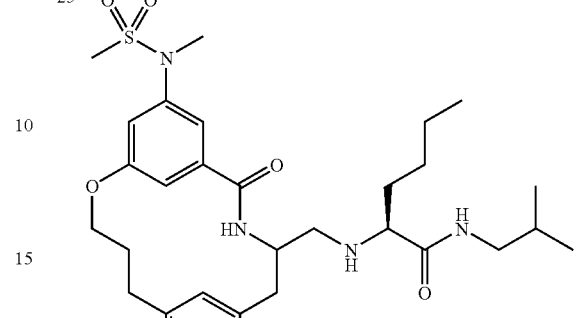 |
| 26 | 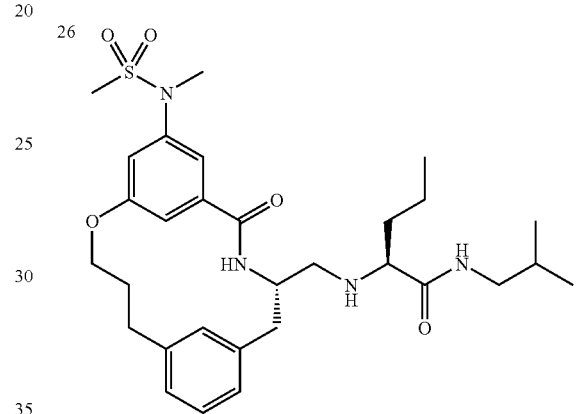 |
| 28 | 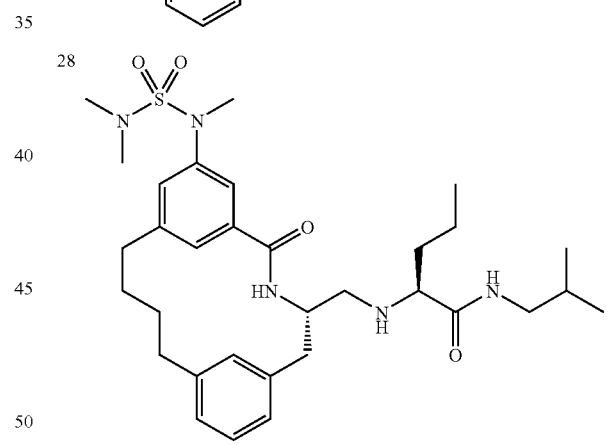 |
| 29 | 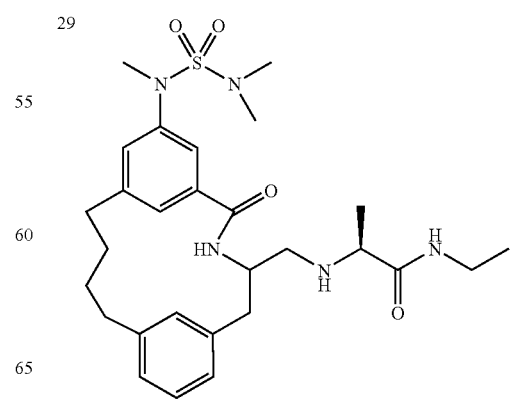 |

-continued
| Ex | Structure |
|---|---|
| 30 | 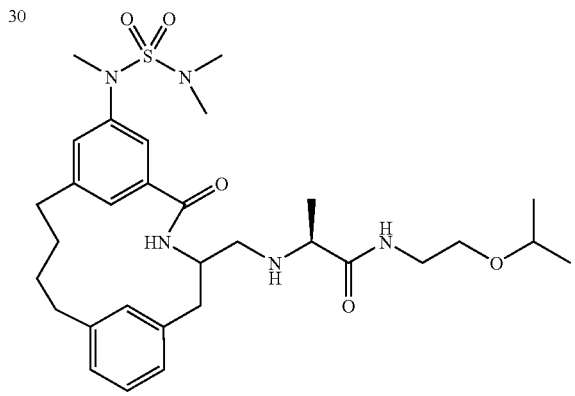 |
| 31 | 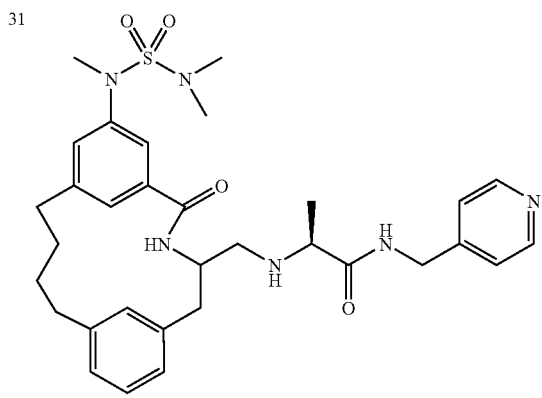 |
| 32 | 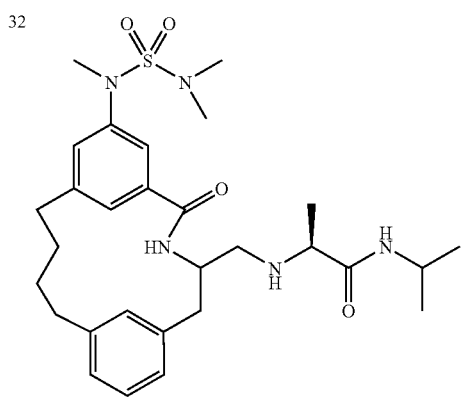 |
-continued
| Ex | Structure |
|---|---|
| 33 | 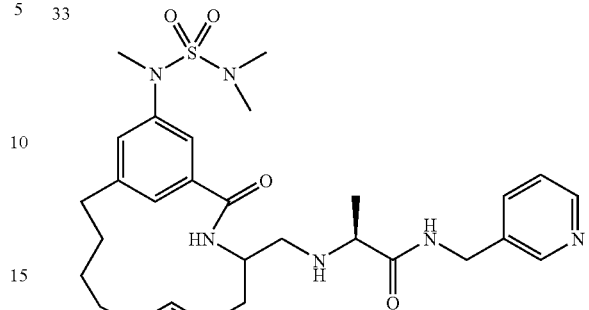 |
| 34 | 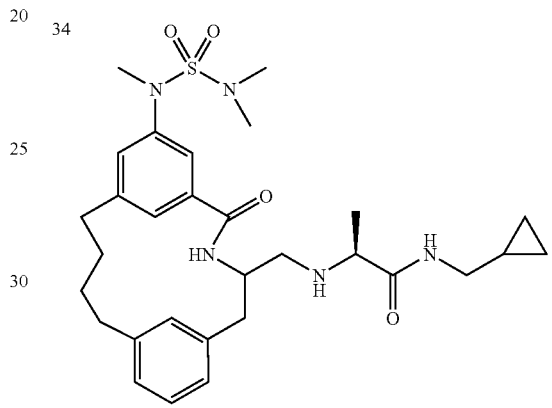 |
| 35 | 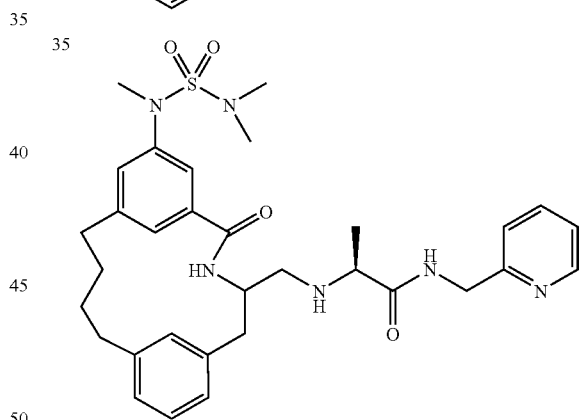 |
| 36 | 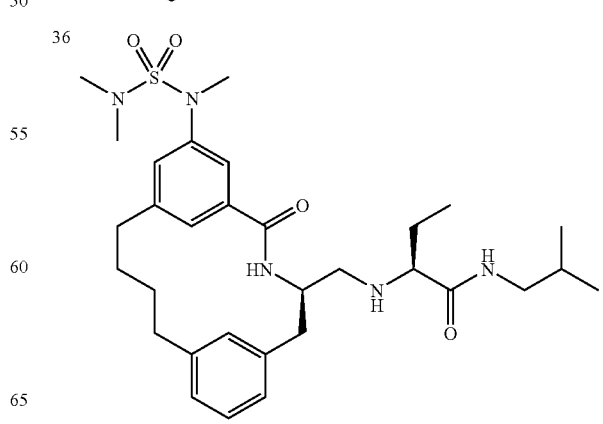 |

| Ex | Structure |
|---|---|
| 37 | 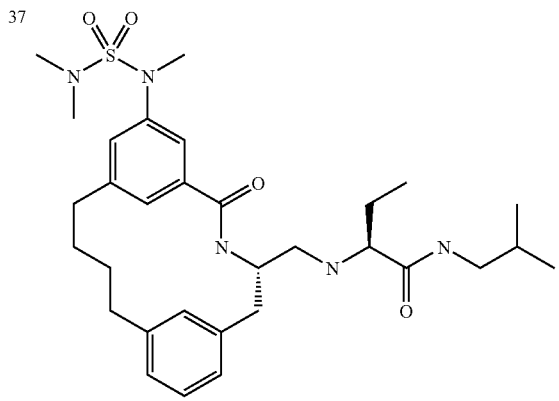 |
or a pharmaceutically acceptable salt thereof.
15. A pharmaceutical composition comprising an effective amount of a compound of claim 1 and a pharmaceutically acceptable carrier.
16. A compound of claim 1 which is
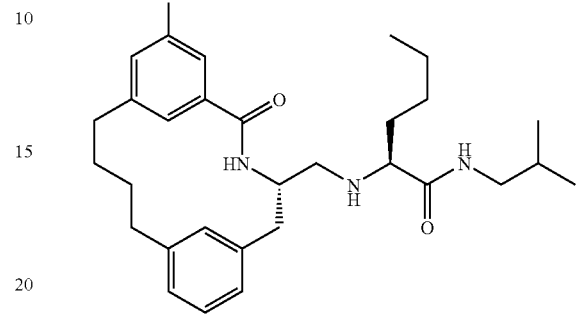
or a pharmaceutically acceptable salt thereof.
* * * * *